Oct. 22, 1963 A. D. CARTWRIGHT, SR Plant Pat. 2,290
ILEX CORNUTA PLANT (CHINESE HOLLY)
Filed April 12, 1962
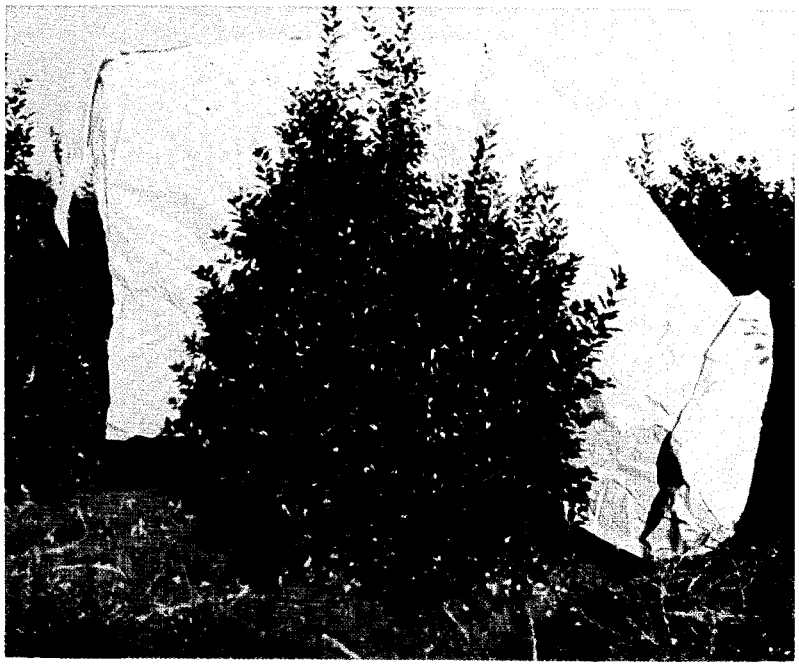
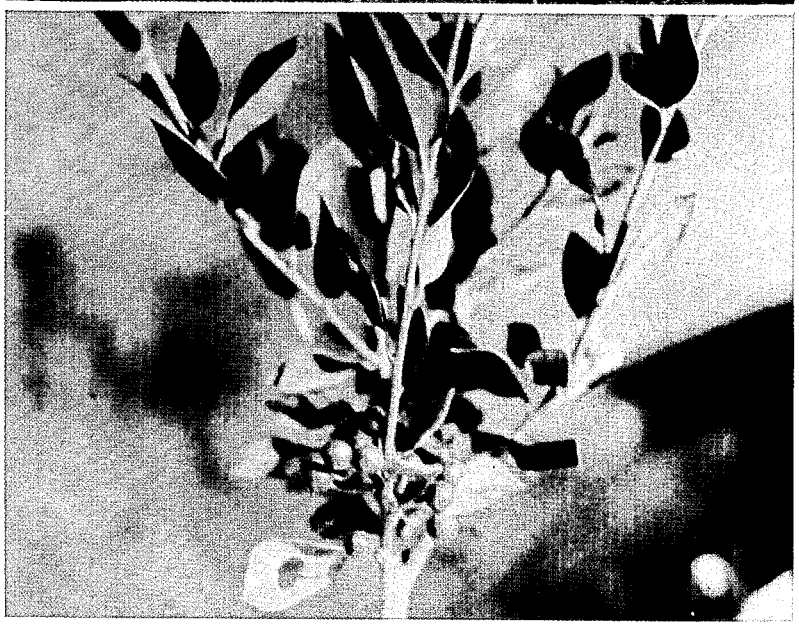
INVENTOR
ALBERT D. CARTWRIGHT, SR.
BY Lamont Johnston
ATTORNEY United States Patent Office Plant Pat. 2,290
Patented Oct. 22, 1963

2,290

*ILEX CORNUTA* PLANT (CHINESE HOLLY)

Albert D. Cartwright, Sr., Collierville, Tenn., assignor to Cartwright Nurseries, Collierville, Tenn., a partnership Filed Apr. 12, 1962, Ser. No. 187,139
1 Claim. (Cl. Plt.—65)

My invention relates to a new and distinct cultivar of Chinese holly plant or *Ilex cornuta*. For many years, we have been growing seedling plants of *Ilex cornuta* to select new improved cultivars. The new plant originated as an open pollinated or chance seedling from plants of *Ilex cornuta* in my nursery in Collierville, Tennessee.

This new cultivar was selected for its ease in propagation, transplanting and the following characteristics:

(1) Long, narrow, dark green leaves.
(2) Dark red berries, borne freely on young plants.
(3) Dense, broad growth habit.
(4) Adaptable to a wide range of soils.
(5) The dark green leaves persist even under adverse growing conditions.

Asexual propagation of this new plant by cuttings, as performed in my nursery at Collierville, Tennessee, shows that this plant reproduces true to form with the above characteristics transmitted through succeeding propagations.

References to color in the following description refer to the Horticulture Colour Charts, volumes I and II, issued by the British Colour Council and the Royal Horticultural Society. Where there are other references to color, the ordinary dictionary meanings of the terms are intended.

The accompanying illustrations show in natural color a typical branch of foliage and berries, and the entire plant of this new variety.

*The Plant*

Growth habit: A dense, broadleaf evergreen plant; branching low to the ground at a young age. Indeterminate habit of growth with profuse lateral branching.

Foliage: Leaves—Glabrous, elliptical oblong, single spine at apex, recolute entire leaf margin, alternate, coriaceous, thick dark lustrous green above, 1½″ to 2¼″ long, and ⅝″ to ¾″ wide; base rounded. The leaves have a slightly distorted twisting of the entire leaf blade.

Color: Mature upper surface, glossy, Spinach Green o960; under surface, Scheeles Green 860/1.

Flowers: Carpellate, usually borne in fascicles, creamy white, April, produced on previous season's growth.

Fruit: Spherical, ¼″ to 5/16″ diameter; stigma—small, discoid, protruding, in clusters 3 to 8, pedicels ½″ to ⅝″ long. Fruit produced readily on young plants.

Color: Blood Red 820. Seeds—4; 3/16″ long.

Disease and pest resistance: Highly resistant to diseases and insects, as observed under field conditions in my nursery and in comparison with other cultivars of *Ilex cornuta*.

Hardiness: Hardy without protection in zones 6*b*, 7, 8, 9, and 10, as shown in the Plant Hardiness Zone Map, Miscellaneous Publication #814, Agricultural Research Service, U.S.D.A. Additional hardiness zones to be determined in the future.

The disease and pest resistance has been demonstrated by growing this new cultivar in my nursery at Collierville, Tennessee, adjacent to other varieties of *Ilex cornuta*. While diseases and insect pests are not too prevalent among *Ilex cornuta* varieties in general, this new cultivar has shown no indication of leaf spot, scale or chlorosis, while these conditions have, in some cases, been encountered in other varieties of *Ilex cornuta* grown nearby. As to hardiness, there has been no winter damage or seasonal damage to plants of this new cultivar in my nursery during the last two seasons. The same observations as to disease and pest resistance and hardiness have been made during the last two seasons by nurserymen growing this new cultivar on an experimental basis in the Memphis, St. Louis and Philadelphia areas.

This new cultivar is easily distinguished from other cultivars of *Ilex cornuta* by the following characteristics:

(1) Color, size and shape of the leaf as outlined above under "Foliage."

(2) Growth habit, particularly the lateral branching and indeterminate growth habits.

(3) Ease of transplanting, determined by experience on an experimental basis with nurserymen in the Memphis, St. Louis and Philadelphia areas.

I claim:

A new and distinct cultivar of *Ilex cornuta* (Chinese holly) plant with combination of features herein shown and described, characterized particularly by the glossy, dark green, elliptical, oblong leaves, and dense, broad habit of growth.

No references cited.